US006235022B1

(12) United States Patent
Hallock et al.

(10) Patent No.: US 6,235,022 B1
(45) Date of Patent: May 22, 2001

(54) RF GENERATOR AND PUMP APPARATUS AND SYSTEM AND METHOD FOR COOLED ABLATION

(75) Inventors: Daniel K. Hallock, Redwood City; Daryl C. Jamgotchian, Sunnyvale, both of CA (US)

(73) Assignee: Cardiac Pathways, Inc, Sunnyvale, CA (US)

( * ) Notice: Subject to any disclaimer, the term of this patent is extended or adjusted under 35 U.S.C. 154(b) by 311 days.

(21) Appl. No.: 08/770,411

(22) Filed: Dec. 20, 1996

(51) Int. Cl.[7] .................................................. A61B 18/18
(52) U.S. Cl. ............................ 606/41; 607/101; 607/105
(58) Field of Search ................................. 607/100–102, 607/104, 105; 606/40, 41, 42, 48–50

(56) References Cited

U.S. PATENT DOCUMENTS

| 5,156,151 | 10/1992 | Imran . | |
|---|---|---|---|
| 5,279,569 | 1/1994 | Neer et al. . | |
| 5,330,518 | * 7/1994 | Neilson et al. | 607/101 |
| 5,334,193 | * 8/1994 | Nardella | 606/41 |
| 5,342,357 | * 8/1994 | Nardella | 606/40 |
| 5,348,554 | * 9/1994 | Imran et al. | 606/41 |
| 5,628,771 | * 5/1997 | Mizukawa et al. | 607/102 |

* cited by examiner

Primary Examiner—Michael Peffley
(74) Attorney, Agent, or Firm—Flehr Hohbach Test Albritton & Herbert LLP

(57) ABSTRACT

A radio frequency generator and pump apparatus for cooled ablation for ablating tissue in the wall of the heart of a patient. An ablation catheter comprising a flexible elongate member has proximal and distal extremities. An ablation electrode. is carried by the distal extremity. An electrical conductor is carried by the flexible elongate member and is coupled to the ablation electrode. A radio frequency generator is coupled to the electrical conductor. The flexible elongate member has a liquid carrying lumen extending from the proximal extremity to the distal extremity and opens into the cavity of the ablation electrode. A pump is coupled to the liquid lumen for supplying a cooling liquid to the lumen and to the ablation electrode. An automatic control apparatus controls the operation of the radio frequency generator and the pump to supply precooling, cooling and post-cooling to the ablation electrode to maintain the ablation electrode at a temperature to prevent excessive heating of the ablation electrode and the surrounding cardiac tissue.

15 Claims, 2 Drawing Sheets

RF GENERATOR AND PUMP APPARATUS AND SYSTEM AND METHOD FOR COOLED ABLATION

This invention relates to an RF generator and pump apparatus and system and method for cooled ablation of cardiac tissue.

The use of cooled ablation for ablating cardiac tissue is disclosed in U.S. Pat. No. 5,348,554. As disclosed therein radio frequency energy for ablation of cardiac tissue is utilized while simultaneously delivering a sterile biocompatible fluid to the ablation electrode of the ablation catheter. in order to obtain the appropriate site for performing an ablation, the mapping of the walls of the chamber of the heart can be carried out by the use of a mapping catheter of the type disclosed in U.S. Pat. No. 5,156,151. As is well known to those skilled in the art, the use of such mapping in ablation procedures is typically used for the treatment of cardiac arrhythmias. A combined RF generator and pump apparatus for performing a cool ablation has heretofore been provided. However, such apparatus has been deficient in providing the precision and control features desired with such apparatus. There is therefore need for a new and improved radio frequency generator and pump apparatus and system and method for performing a cooled ablation procedure.

In general, it is an object of the present invention to provide a radio frequency generator and pump apparatus and system and method for automatically controlling the cooled ablation of cardiac tissue.

Another object of the invention is to provide an apparatus, system and method of the above character in which a high degree of automation is utilized.

Another object of the invention is to provide an apparatus, system and method of the above character in which closed loop controls are utilized.

Another object of the invention is to provide a radio frequency generator and pump apparatus which can be used with different types of catheters for performing cooled ablation.

Another object of the invention is to provide an apparatus, system and method of the above character which incorporates a number of safety features.

Another object of the invention is to provide an apparatus, system and method of the above character in which a progress bar is utilized to provide information to the user about the status of an ablation procedure.

Additional objects and features of the invention will appear from the following description in which the preferred embodiment is set forth in detail in conjunction with the accompanying drawing.

Figure 1:
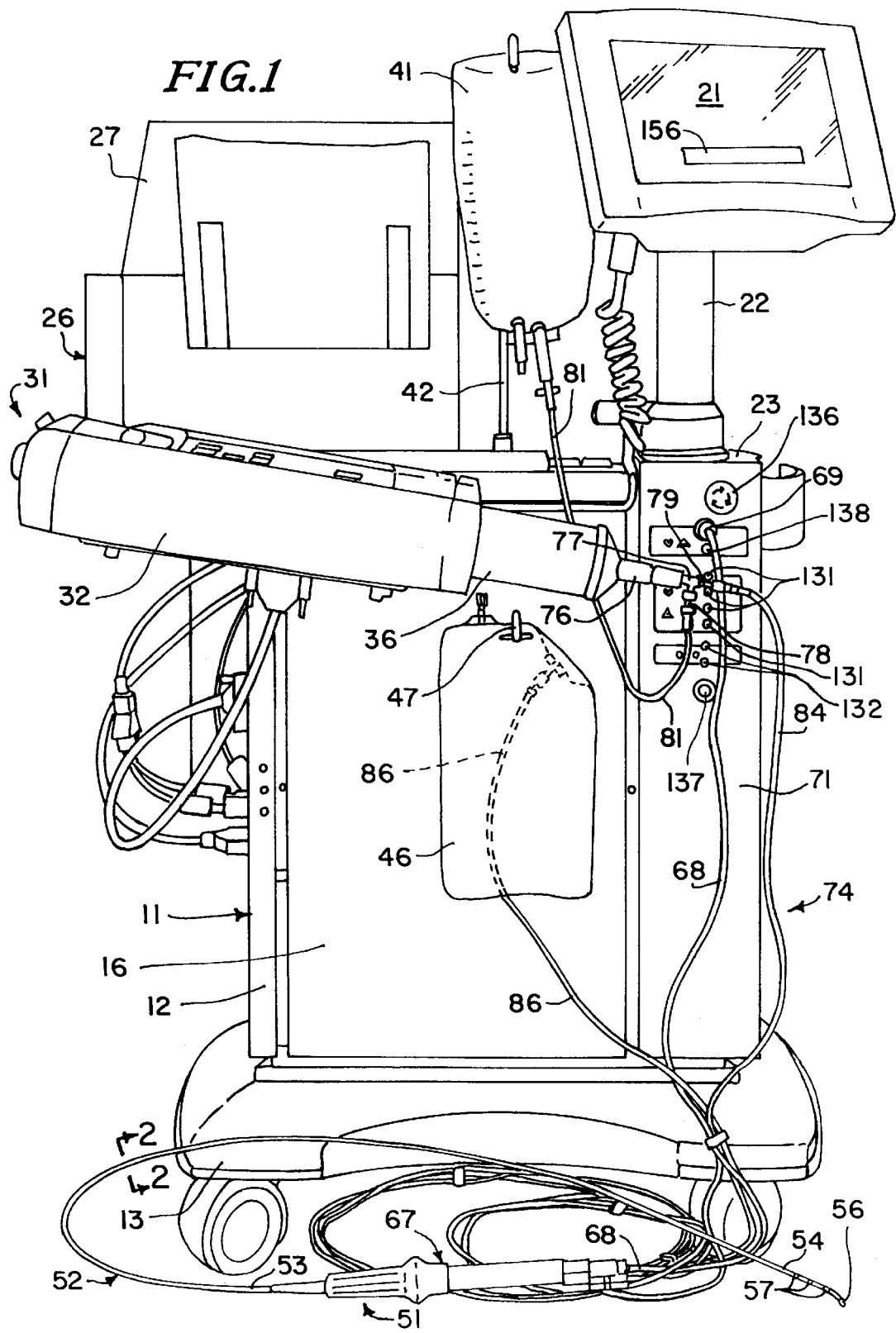
FIG. 1 is a front elevational view of a RF generator and pump apparatus and system for cooled ablation incorporating the present invention and used for performing the method of the present invention.

In general the RF generator and pump apparatus for cooled ablation for ablating tissue in the wall of a heart of a patient is comprised of an ablation catheter which has a flexible elongate member having proximal and distal extremities. An ablation electrode is carried by the distal extremity. An electrical conductor is carried by the flexible elongate member and is coupled to the ablation electrode. A radio frequency generator is coupled to the electrical conductor for supplying radio frequency energy to the ablation electrode. The flexible elongate member also has a liquid carrying lumen extending from the proximal extremity to the distal extremity and opening into the cavity of the ablation electrode. A pump is coupled to the liquid carrying lumen for supplying a cooling liquid to the lumen and to the ablation electrode. Control means is provided for automatically controlling the operation of the RF generator and the pump to maintain the cooled electrode at a temperature to prevent excessive heating of the electrode and the surrounding cardiac tissue.

More specifically the RF generator and pump apparatus 11 and system for cooled ablation consist of a cabinet 12 which is mounted on a wheeled platform 13. The cabinet 12 contains the automatic control circuitry which is shown in block diagram form in FIG. 2. The control circuitry is accessible through a front door 16 provided on the cabinet 12. A touch screen 21 is mounted on a pedestal 22 affixed to the top 23 of the cabinet 12. The touch screen 21 is mounted on the pedestal 22 in a conventional manner so that it can be tilted and rotated by the user so that the touch screen 21 can face the user. A printer 26 is also mounted on the top 23 on the left hand side of the cabinet 12 as viewed in FIG. 1. The printer 26 can be of a conventional type as for example a Hewlett-Packard DeskJet 340 printer. The printer 26 is provided with a paper tray 27.

Figure 2:
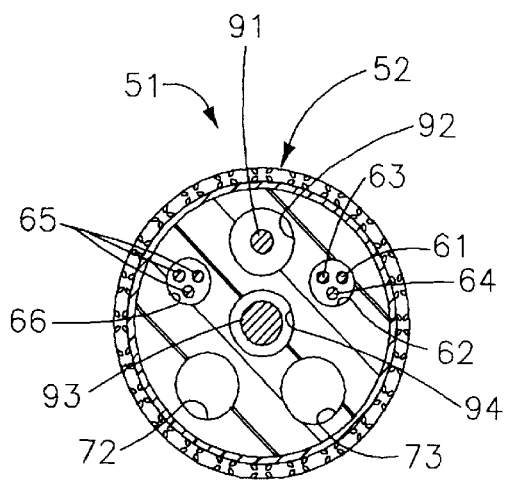
FIG. 2 is a cross-sectional view taken along the line 2—2 of FIG. 1.

A pump assembly 31 is provided as a part of the apparatus 11 and as shown is suitably mounted on the upper left hand portion of the cabinet 12 as shown in FIG. 1. The pump assembly 31 includes a power head 32 which is mounted on a swivel (not shown) secured to the cabinet 12 which permits tilting of the power head 32 about a horizontal axis. The pump assembly 31 also includes a replaceable syringe 36 of a suitable size as for example 200 ml which is front end mounted on the power head 32. The power head 32 and the syringe 36 forming a part of the pump assembly 31 are conventional and can be of the type described in U.S. Pat. No. 5,279,569 supplied by the Liebel-Flarsheim Company of Cincinnati, Ohio. The pump assembly 31 includes the electronics necessary to calibrate the power head 32 position and pressure when controlled interactively by the user through the touch screen 21 and the electronics contained in the cabinet 12.

A reservoir bag 41 is provided for supplying a sterile biocompatible liquid and is carried by a post 42 also mounted on the top 23 of the cabinet 12. A liquid disposal bag 46 is also provided which is secured to a hook 47 mounted on the front door 16.

The apparatus 11 also includes a closed-circuit cooled ablation catheter of a conventional type as described in U.S. Pat. No. 5,348,554 and of a suitable size, such as 7-French. However, it should be appreciated that other catheters of the type disclosed in U.S. Pat. No. 5,348,554 can be utilized, as for example of an open-loop type in which the cooling liquid passes through or over the ablation electrode and into the human body and is not returned. The apparatus of the present invention can also be used with linear lesion ablation catheters of the type described in co-pending application Ser. No. 08/611,656 filed Mar. 6, 1996.

The catheter 51 shown in FIG. 1 consists of a flexible elongate member 52 formed of plastic and having proximal and distal extremities 53 and 54. A tip ablation electrode 56 and a plurality of spaced-apart ring electrodes 57 formed of a conductive metal are carried by the distal extremity 54. The tip electrode has its interior surface exposed to a cavity (not shown) provided in the electrode. An electrical conductor 61 (see FIG. 2) is carried by the flexible elongate member 52 and is secured to the ablation electrode and extends to the proximal extremity. The conductor 61 extends through a lumen 62 as do two thermocouple wires 63 and 64. The wires 63 and 64 are connected to a thermocouple (not shown) carried by the distal extremity of the flexible elongate member 52. Additional conductors 65 extending through another lumen 66 are connected to the ring electrodes 57.

A control handle 67 is mounted on the proximal extremity of the flexible elongate member and includes means (not shown) for rotating the flexible elongate tubular member 52 and also for causing bending of the distal extremity of the flexible elongate member 52. A cable 68 connects the handle 67 to an RF ablation output 69 provided on a front panel 71 of the cabinet 12 disposed to the right-of the front door 16 as viewed in FIG. 1.

The flexible elongate tubular member 52 also includes first and second liquid carrying lumens 72 and 73 of a suitable size, such as 0.020" in diameter extending from the proximal extremity 53 to the distal extremity 54. The distal extremities of lumens 72 and 73 open into the cavity (not shown) of the ablation electrode 56. Tubing is provided for making connections to the first and second lumens 72 and 73 and consists of a tube set 74 removably secured to an outlet 77 of the syringe 36. A dual check valve 77 is provided with first and second legs 78 and 79 of which the first leg 78 serves as a liquid inlet connected by tubing 81 to the reservoir bag 41. The second or other leg 79 is an outlet leg and is connected by tubing 84 to the first liquid carrying lumen 72 of the ablation catheter 51. The second liquid carrying lumen 72 is connected by tubing 86 to the liquid disposal bag 46. The dual check valve assembly is of a suitable conventional type as one supplied by B. Braun, Part No. S540108. The flexible elongate tubular member 52 also carries a pull wire 91 extending through a lumen 92 connected to the control handle 67 and a shape memory element 93 extending through a lumen 94 to provide spring back for the distal extremity of the catheter 51 when the pull wire 91 is released.

Figure 3:
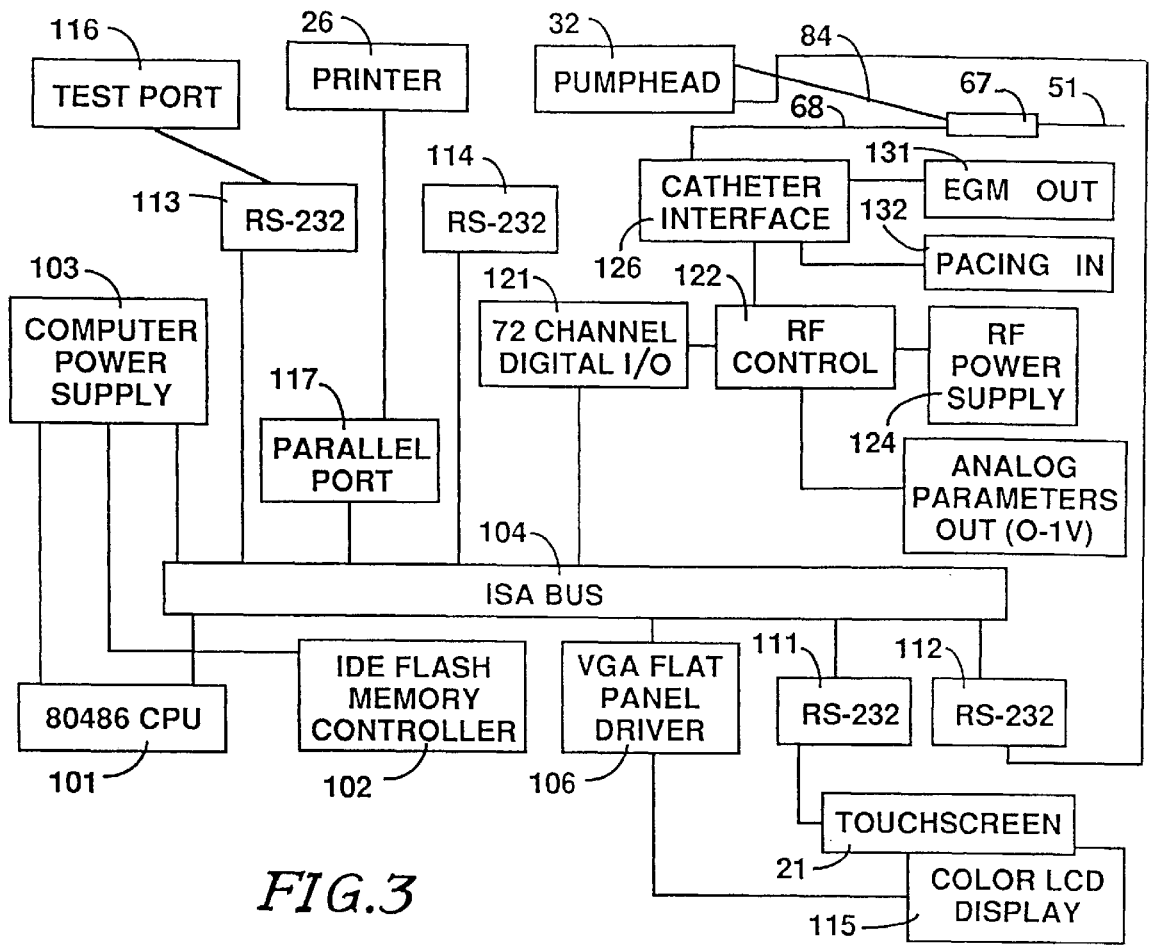
FIG. 3 is a block diagram of the electronics and the electrical control circuitry utilized in the apparatus and system of the present invention.

The electrical circuitry which is utilized in the apparatus 11 is shown in FIG. 3 and is mounted on a computer board (not shown) provided in the cabinet 12. A microprocessor 101 of a suitable type as for example an 80486 CPU supplied by Intel is mounted on the computer board. The microprocessor 101 is controlled by an IDE flash memory controller 102 of a conventional type in the form of a 4 megabyte EPROM card supplied by Sandis K of Santa Clara, Calif. A computer power supply 103 supplies power to the CPU 101 as well as the flash memory 102 to an ISA bus 104.

A separate radio frequency power supply (not shown) is provided within the cabinet 12 and is connected to the radio frequency power output 69 hereinbefore described. The ISA Bus 104 is provided for supplying power to a VGA flat panel driver 106 and for supplying power to RS232 ports 111, 112, 113 and 114. The VGA flat panel driver 106 is connected to a color LCD display 115. The RS232 port 111 is connected to the touch screen 21. The RS232 port 112 is connected to the pump head 32. The pump head 32 as explained previously is of a conventional type and includes an independent CPU with communication being established between the CPU of the pump head and the CPU 101 through the serial port 112. The port 113 is connected to a test port 116. The ISA Bus 104 is also connected to a parallel port 117. The ISA Bus 104 is also connected to a 72 channel digital I/O card 121 which interfaces with RF control 122. The RP control 122 controls the radio frequency power supply 124 which is connected to the RF ablation output 69 hereinbefore described. The RF control 122 is connected to a catheter interface 126 which is connected by the cable 68 to the handle 67 of the ablation catheter 51. The catheter interface 122 is also connected with EGM out terminals 131 shown on the front panel 71 and which are connected to the ring electrodes 57 and the tip electrode 56. The interface 122 is connected to pacing in terminals 132 provided on the front panel 71. An emergency stop button 136 and a power on-off button 137 are also provided on the front panel 71. A terminal 138 is provided on the front panel 71 for connection to a ground pad (not shown) placed on the patient.

A pump console (not shown) normally used to control the pump operation and calibration is not incorporated as a part of the system because its functionality is included in the electronics and software contained in the cabinet 12. This simplifies the pump assembly and makes it possible to calibrate the pump assembly 31 from the touch screen 21 carried on the cabinet 12.

Operation and use of the RF generator and pump apparatus and system for performing a cooled ablation utilizing the method of the present invention may now be briefly described as follows. Let it be assumed that it is desired to perform an ablation procedure with the apparatus and system hereinbefore described and that the site in the wall 151 of the heart 152 in which cardiac tissue is to be ablated has been ascertained previously by the use of a mapping procedure such as described in U.S. Pat. No. 5,156,151 on a patient which has been suffering from ventricular tachycardia with the use of a mapping catheter introduced through a guide catheter inserted through the femoral artery leading into the left ventricle of the patient's heart. Let it be assumed by the mapping procedure hereinbefore carried out it has been found that the desired location at which it is desired to perform an ablation to treat the cardiac arrhythmia has been located.

Figure 4:
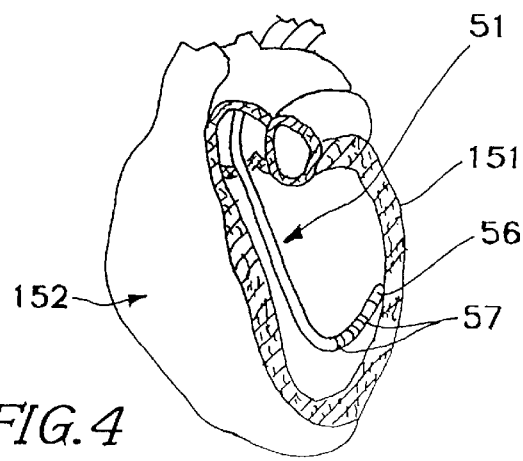
FIG. 4 is a representation of a human heart showing of a cooled ablation catheter in accordance with the present invention.

In preparation of the apparatus 11 for use in a procedure, the tubing utilized is connected in the manner hereinbefore described and the syringe 36 is filled with the desired liquid as for example a saline solution. Care should be taken so that no air is introduced into the tubing or into the syringe 36. To ensure that no air is introduced by the syringe 36, the power head 32 is tilted so that the syringe 36 is inclined downwardly. If by chance air does become entrapped within the syringe, it is merely necessary that the power head be tilted so that the syringe extends upwardly so that any air within the syringe will come to the top of the syringe after which it can be ejected through the tubing 84 to ensure that all air is expelled before the ablation catheter 51 is introduced into the patient. The ablation catheter 51 is introduced into the femoral artery and through the guiding catheter into the left ventricle of the heart in a conventional manner by observation of the advancement of the same under fluoroscopy and by use of the handle 67 to move the distal extremity carrying the tip electrode 56 until the tip electrode 56 is positioned in contact with the wall 151 of the heart 156 in the location at which it is desired to perform a radio frequency ablation as shown in FIG. 4.

Assuming that the apparatus 11 is now ready for an ablation procedure, the operator presses an "Enable" button appearing on the touch screen 21 to start the ablation procedure. A dialogue box then appears on the touch screen. The operator is given two choices whether or not to proceed with the ablation procedure. The operator is requested to check whether or not there is any air in the system. If there is not after visual inspection by the operator, the operator presses an "OK" button to continue the process. If air is found in the system, the operator presses the "Cancel" button. Assuming that the "OK" button has been pressed, the "Enable" button is now labeled as "Pumping" to indicate that a pump priming process is under way in the apparatus. The progress of the pumping is displayed in a progress bar 156 appearing at the lower portion of the touch screen 21. This progress bar displays how much progress (relative to time) has occurred in the pump priming process. This progress bar is very helpful to the operator because it tells the operator that something is occurring while the operator is waiting for the next function to be performed in the method.

After the pump priming process has been completed which typically takes approximately 15 seconds, the progress bar fills up to indicate that the pump priming phase has been completed. During this pump priming phase, the injector of the pump assembly 31 causes the syringe 36 to inject liquid into the ablation catheter 51 at a controlled rate as for example a rate of 0.6 ml per second to cause the liquid to flow through the first lumen 72 into the cavity of the ablation electrode 56 to cool the ablation electrode prior to the application of RF energy. Typically this cooling is accomplished by the use of a cooling liquid which is at room temperature. However, it should be appreciated if desired in accordance with the present invention the liquid utilized can be pre-cooled to a lower temperature as for example a temperature ranging from 5 to 10° C.

When the pumping progress bar 156 has filled up, a "start" button on the touch panel 21 is illuminated. The operator can then press the "start" button to start the ablation procedure. As soon as the "start" button is pressed, it changes to a "stop" button indicating that the system will continue the ablation for the specified duration heretofore provided on the therapy screen of the touch screen 21. Any desired power setting and time can be programmed into the touch panel. The maximum power setting with the apparatus of the present invention is 50 watts with a maximum duration of 295 seconds. At the time that the "start" button is pressed, radio frequency power from the RF power supply 124 is supplied through the RF ablation output 68 through the cable 67 to the large area ablation tip electrode 56. Ablation is continued in the programmed manner until the timing has reached 0 after which ablation is terminated. Alternately, the operator can manually terminate the procedure at any time by depressing the "stop" button. When the "stop" button is pressed or when the apparatus times out automatically, radio frequency power being supplied by the radio frequency power supply 124 is terminated.

In accordance with the present invention, temperature and impedance encountered by the electrode 56 are measured and are displayed on the touch screen 21. This information can be obtained in a conventional manner, such as by providing a thermocouple (not shown) in the distal extremity 54 of the flexible elongate member 52. The thermocouple is connected by conductors extending through the flexible elongate member 52 through the cable 68 to the touch panel 21. The upper limits of temperature and the upper and lower impedance limits can be set by use of the touch panel 21 which is provided with the capability of shutting down the apparatus and system in the event the temperature or impedance are out of range.

During the time that cooling liquid is being introduced into the ablation catheter 51, the system continues to monitor the status of the power head 32 and the syringe 36, as for example as often as four times a second. At the same time, the controller is continuously monitoring the remaining volume of liquid in the syringe 36 and the flow of liquid being delivered by the syringe. If at any time, the control system detects that the syringe volume is too low to complete the ablation procedure or if a flow rate is too high or too low, the ablation procedure will be aborted. Thus there is provided a closed loop system for continuously monitoring syringe volume and flow rate.

In the event the ablation procedure is terminated either automatically by the closed loop feedback hereinbefore described or manually by the operator by operation of the "stop" button, the application of radio frequency energy to the ablation electrode 56 is immediately terminated. However, the control system permits the pump assembly 31 to continue operation for a suitable period of time, as for example five additional seconds to provide additional cooling to remove any residual heat in the ablation electrode 56 after radio frequency energy has been terminated. After this five-second period expires, an automatic stop command is supplied to the pump assembly 31 which causes the pump assembly 31 to stop injecting liquid into the ablation catheter.

At this time, the system checks the volume indicator of the syringe 36 to ascertain whether or not there is sufficient liquid in the syringe 36 to complete the ablation procedure or to perform another ablation procedure. If there is inadequate volume of liquid in the syringe, a Retract command is sent to the power head 32 to cause the syringe to be filled up with liquid from the reservoir bag 41. The control system has been provided with automatic retraction when an ablation procedure has been terminated to ensure that sufficient liquid is in the syringe for another ablation procedure. This ensures that there will always be adequate liquid in the syringe for performing an ablation procedure after an ablation procedure has been terminated for any reason.

From the foregoing it can be seen that the RF generator and pump apparatus and system for performing a cooled ablation in accordance with the method of the present invention is accomplished by delivering radio frequency energy for ablation through the ablation catheter while simultaneously delivering a sterile biocompatible fluid i.e. a saline solution to the ablation electrode of the ablation catheter. The radio frequency generator delivers radio frequency energy in a constant power output up to 50 watts of power which is delivered through the catheter ablation electrode 56 and returns through a return patch (not shown) on the patient's skin. The saline solution is circulated through the ablation catheter and into the cavity of the ablation electrode during the time that radio frequency energy is being supplied to the ablation electrode. During the delivery of radio frequency energy through the ablation electrode, the radio frequency energy is introduced into the cardiac tissue from the large dispersal tip electrode 56 and heats the tissue due to resistive heating from current passing from the ablation electrode to the return patch electrode on the patient's outer skin. It is this heating that causes cardiac tissue to desiccate and a lesion to be formed in the myocardium of the heart. This lesion is made to stop the arrhythmia of the heart of the patient by blocking the propagation of the arrhythmia in the tissue. It is desirable to prevent excessive heating of the ablation electrode which if uncontrolled may cause coagulation of blood on the ablation electrode which can cause an increase in impedance and an undesirable dropping off of the conductive heating. These effects are monitored by measuring temperature and impedance at the electrode as controlled by removing heat from the ablation electrode and the surrounding area by introducing the cooling sterile fluid which is circulated through the ablation catheter and over the ablation electrode during the application of radio frequency energy.

The radio frequency generator of the present invention accepts temperature input from a thermocouple located in the ablation electrode of the ablation catheter. The radio frequency generator is connected to the ablation electrode and up to three other catheter electrodes on the distal extremity of the ring electrodes of the ablation catheter. Intracardiac electrogram (EGM) signals from these electrodes may be used with other diagnostic and monitoring equipment. As explained previously, the apparatus and system of the present invention permits connection of a pacing stimulator which passes pacing pulses to the ablation electrode and the next most distal electrode of the ablation catheter. The apparatus and system also has provision for connections for external monitoring and recording equipment connected directly to the intracardiac electrogram (EGM) signals from the ablation electrode and three other (typically ring type) electrodes 57 of the cooled catheter.

The adjustable parameters for the apparatus and system of the above invention are power ranging from 1 to 50 watts with incremental adjustments of 1 watt. The duration can be from 5 to 295 seconds with increments of 5 seconds and a typical setting of 30 seconds. The maximum impedance limits can be from 100 to 500 ohms with an increment of 5 ohms and with a typical setting of 200 ohms. The minimum impedance limit can range from 50 to 200 ohms in increments of 5 ohms with a typical setting of 50 ohms. The maximum temperature in the power mode can range from 20–110° C. with 1° C. increments with a typical setting of 100° C. The maximum duration can range from 0 to 295 seconds with increments of 1 second and a typical setting of 120 seconds.

The AC power input for the apparatus can be the typical 110 volt AC 50–60 Hertz. The radio frequency power output can have a frequency of 500 kHz to within 5%. The syringe can be of a suitable size as for example 200 ml and have a fill rate of less than 50 seconds in forward or reverse and a flow rate which can be preset to 0.6 ml per second and pressure limits preset to 300 psi.

In accordance with the present invention, a two step button selection is required to start ablation or in other words to begin power output. This prevents a single inadvertent operator selection from starting the ablation. The ablation start sequence includes a pause in which it requests the operator to visually inspect the syringe and the fluid inlet tubing. The operator must manually confirm the inspection on the touch screen prior to the pump starting and prior to enabling the ablation delivery sequence. An emergency stop button 136 is provided for disconnecting the electronics from the catheter output. The emergency switch must be completely disengaged to resume normal operation. The operator typically selects a temperature limit for the catheter temperature sensor during a constant power output ablation. This reduces the risk of the ablation electrode reaching a temperature that would cause an impedance rise during the ablation procedure. The operation of the pump is continuously monitored during delivery of ablation energy. Power delivery is stopped if the internally monitored communication with the pump fails or the correct pumping parameters are not confirmed or there is insufficient volume left in the syringe. For example, if the pump flow rate is not within the correct range or if the pump pressure limit is exceeded, delivery of ablation energy is halted and the operator is informed of a pump malfunction. The control system also stops power delivery in a constant power mode if the internally monitored power output is more than 5 watts above the selected target value. This permits for minor changes in circuit performance but guards against larger increases in power output due to other conditions as for example an impedance rise. The operator may select a maximum impedance limit for the ablation procedure which if exceeded will disable the power output. A specific duration for the ablation can be selected which gives the operator ability to select variable length ablations but provides an upper length time limit. The control system emits an audible tone while radio frequency power is being applied which alerts the operator to the fact that ablation power output is occurring. In addition an ablation in progress light is on while the radio frequency power is being applied.

What is claimed is:

1. A radio frequency generator and pump apparatus for cooled ablation for ablating tissue in the wall of the heart of a patient, an ablation catheter comprising a flexible elongate member having proximal and distal extremities, an ablation electrode formed of a conductive material and carried by the distal extremity, said ablation electrode having a cavity therein, an electrical conductor carried by the flexible elongate member and coupled to the ablation electrode, a radio frequency generator coupled to said electrical conductor, said flexible elongate member having a liquid carrying lumen extending from the proximal extremity to the distal extremity and opening into the cavity of the ablation electrode, a pump coupled to the liquid lumen for supplying a cooling liquid to the lumen and to the cavity of the ablation electrode and automatic control means for controlling the operation of the radio frequency generator and the pump to supply pre-cooling, cooling and post-cooling in succession without interruption to the ablation electrode to maintain the ablation electrode at a temperature to prevent excessive heating of the ablation electrode and in the wall of the heart when the ablation electrode is in contact with the wall of the heart.

2. Apparatus as in claim 1 together with a radio frequency generator and pump apparatus for cooled ablation for ablating tissue in the wall of the heart of a patient, an ablation catheter comprising a flexible elongate member having proximal and distal extremities, an ablation electrode carried by the distal extremity, said electrode being formed of a conductive material and having a cavity therein, an electrical conductor carried by the flexible elongate member and coupled to the ablation electrode, a radio frequency generator coupled to said electrical conductor, said flexible elongate member having a liquid carrying lumen extending from the proximal extremity to the distal extremity and opening into the cavity of the ablation electrode, a pump coupled to the liquid lumen for supplying a cooling liquid to the lumen and to the ablation electrode, automatic control means for controlling the operation of the radio frequency generator and the pump to supply pre-cooling, cooling and post-cooling in succession without interruption to the ablation electrode to maintain the ablation electrode at a temperature to prevent excessive heating of the ablation electrode and tissue in the wall of the heart when the ablation electrode is in contact with the wall of the heart, a reservoir connected to said pump and carrying additional cooling liquid for use by said pump and a container, said flexible elongate member having an additional liquid carrying lumen extending from the proximal extremity to the distal extremity and being in communication with the cavity of the ablation electrode and tubing connecting the additional liquid carrying lumen to the container so that liquid introduced from the pump passes through the first named lumen into the cavity and theme into the additional lumen and into the container.

3. Apparatus as in claim 2 wherein said control means includes a touch screen having a progress bar thereon and giving indication of the priming of said pump during pre-cooling of the ablation electrode.

4. Apparatus as in claim 1 wherein said control means includes means for repeatedly checking to ascertain the flow rate of liquid from the pump and at the same time ascertaining the remaining volume of liquid in the pump and means for terminating the ablation procedure in the event the flow rate of liquid from the pump is outside predetermined limits.

5. Apparatus as in claim 1 together with A radio frequency generator and pump apparatus for cooled ablation for ablating tissue in the wall of the heart of a patient, an ablation catheter comprising a flexible elongate member having proximal and distal extremities, an ablation electrode carried by the distal extremity, said ablation electrode being formed of a conductive material and having a cavity therein, an electrical conductor carried by the flexible elongate member and coupled to the ablation electrode, a radio frequency generator coupled to said electrical conductor, said flexible elongate member having a liquid carrying lumen extending from the proximal extremity to the distal extremity and opening into the cavity of the ablation electrode, a pump coupled to the liquid lumen for supplying a cooling liquid to the lumen and to the ablation electrode and automatic control means for controlling the operation of the radio frequency generator and the pump to supply pre-cooling, cooling and post-cooling in succession without interruption to the ablation electrode to maintain the ablation electrode at a temperature to prevent excessive heating of the ablation electrode and tissue in the wall of the heart when the ablation electrode is in contact with the wall of the heart, a reservoir connected to said pump and carrying additional cooling liquid for use by said pump and automatic means for causing a refilling of the pump from the reservoir as soon as it is ascertained that there is inadequate volume of liquid in the pump to complete an ablation procedure.

6. A method for performing ablation of tissue in the wall of the heart of a patient utilizing a radio frequency generator and a pump apparatus and an ablation catheter comprising a flexible elongate member having proximal and distal extremities, an ablation electrode carried by the distal extremity, said electrode being formed of a conductive material and having a cavity therein and an electrical conductor carried by the flexible elongate member and coupled to the ablation catheter in which the ablation catheter has first and second lumens extending from the proximal to the distal extremity and in communication with the cavity in the electrode and a cooling liquid, the method comprising introducing the ablation catheter into the heart and into contact with the wall of the heart of the patient, supplying radio frequency energy to the ablation electrode to ablate tissue in the wall of the heart, terminating the application of radio frequency energy to the ablation electrode and operating the pump apparatus to supply continuously without interruption a cooling liquid through said first lumen and to the ablation electrode to pre-cool the ablation electrode prior to the application of radio frequency energy, to cool the electrode during the application of radio frequency energy and to cool the electrode after the application of radio frequency energy and removing the ablation catheter from the patient.

7. A method as in claim 6 further including the step of providing a visual display during the precooling of the ablation electrode.

8. A method as in claim 6 further including the steps of periodically checking the flow rate of liquid from the pump and ascertaining therefrom whether or not the flow of liquid from the pump is within predetermined limits and terminating the ablation procedure when the flow rate is outside the predetermined limits.

9. A method as in claim 6 wherein the pump apparatus includes a predetermined volume of a cooling liquid together with the step of ascertaining the remaining volume of liquid in the pump apparatus and causing the pump to be refilled with a cooling liquid when the volume of liquid in the pump is inadequate to complete an ablation procedure.

10. An ablation apparatus for ablating tissue in the wall of the heart of a patient comprising an ablation catheter having a flexible elongate member with proximal and distal extremities, an ablation electrode carried by the distal extremity of the flexible elongate member, said electrode being formed of a conductive material and having a cavity therein, an electrical conductor carried by the flexible elongate member and coupled to the ablation electrode, a radio frequency generator coupled to said electrical conductor, said flexible elongate member having a liquid carrying lumen extending from the proximal to the distal extremity and opening into said cavity of the electrode, a pump coupled to the lumen for use with a cooling liquid and automatic control means for controlling the operation of the radio frequency generator and said pump to continuously supply said cooling liquid to the lumen and ablation electrode at a preset, substantially constant flow rate before, during and after ablation in order to provide pre-cooling, cooling and post-cooling of said ablation electrode in succession without interruption and maintain said electrode at a temperature to prevent excessive heating of the ablation electrode and the tissue in the wall of the heart when the ablation electrode is in contact with the wall of the heart.

11. An apparatus as in claim 10 wherein said control means includes means for simultaneously monitoring the pressure and volume of liquid in said pump and means for terminating the ablation procedure in the event the pressure of liquid in said pump is outside predetermined limits.

12. An apparatus as in claim 11 wherein said control means further includes means for terminating the ablation procedure in the event the volume of liquid in said pump is outside predetermined limits.

13. A method for performing ablation of tissue in the wall of the heart of a patient utilizing a cooling liquid and an ablation apparatus having an ablation catheter, said ablation catheter having a flexible elongate member with proximal and distal extremities, an ablation electrode carried by the distal extremity of the flexible elongate member, said electrode being formed of a conductive material and having a cavity therein, an electrical conductor carried by the flexible elongate member and coupled to the ablation electrode, a radio frequency generator coupled to said electrical conductor, said flexible elongate member having a liquid carrying lumen extending from the proximal to the distal extremity and opening into said cavity of the electrode and a pump coupled to the lumen for use with a cooling liquid, the method comprising introducing the ablation catheter into the heart and into contract with the wall of the heart of the patient, operating the pump to continuously supply without interruption a cooling liquid to the lumen and ablation electrode at a preset, substantially constant flow rate before ablation in order to pre-cool said electrode, continuing to operate the pump to continuously supply without interruption a cooling liquid to the lumen and ablation electrode at a preset, substantially constant flow rate in order to continue cooling said electrode while simultaneously supplying radio frequency energy to the ablation electrode to ablate tissue in the wall of the heart, terminating the application of radio frequency energy to the ablation electrode while continuing to supply cooling liquid to the ablation electrode at a preset, substantially constant flow rate for a period of time in order to post-cool the ablation electrode and removing the ablation electrode from the patient.

14. A method as in claim 13 together with the step of periodically monitoring the pressure and volume of cooling liquid in said pump in order to ascertain whether or not the pressure and volume in said pump are within predetermined limits and terminating the ablation procedure when the pressure is outside the predetermined limits.

15. A method as in claim 14 together with the step of terminating the ablation procedure when the volume is outside the predetermined limits.

* * * * *